United States Patent
de Souza et al.

(10) Patent No.: US 6,664,267 B1
(45) Date of Patent: Dec. 16, 2003

(54) CRYSTALLINE FLUOROQUINOLONE ARGININE SALT FORM

(75) Inventors: Noel J. de Souza, Mumbai (IN); Prasad K Deshpande, Aurangabad (IN); Milind C. Shukla, Aurangabad (IN); Siddiqui M Jaweed Mukarram, Aurangabad (IN); Dilip Ganesh Kulkarni, Aurangabad (IN); Ansari Azizur Rahman, Aurangabad (IN); Ravindra D Yeole, Aurangabad (IN); Mahesh V Patel, Aurangabad (IN); Shrikant V Gupte, Aurangabad (IN)

(73) Assignee: Wockhardt Limited, Mumbai (IN)

( * ) Notice: Subject to any disclaimer, the term of this patent is extended or adjusted under 35 U.S.C. 154(b) by 0 days.

(21) Appl. No.: 10/156,685

(22) Filed: May 28, 2002

(51) Int. Cl.⁷ .................. C07D 455/04; A61K 31/4375; A61P 31/04
(52) U.S. Cl. .................. 514/294; 546/94; 424/451; 424/456; 424/461; 424/474; 424/489
(58) Field of Search ............................... 514/294; 546/94

(56) References Cited

U.S. PATENT DOCUMENTS

| | | | |
|---|---|---|---|
| 3,924,042 A | 12/1975 | Gerster et al. | 424/258 |
| 3,984,403 A * | 10/1976 | Fujisawa et al. | 540/221 |
| 3,985,882 A | 10/1976 | Gerster et al. | 424/258 |
| 4,051,247 A | 9/1977 | Schuppan et al. | 424/258 |
| 4,382,892 A | 5/1983 | Hayakawa et al. | 260/243.3 |
| 4,399,134 A * | 8/1983 | Ishikawa et al. | 514/228.2 |
| 4,404,207 A | 9/1983 | Stern et al. | 424/258 |
| 4,416,884 A | 11/1983 | Ishikawa et al. | 424/250 |
| 4,443,447 A | 4/1984 | Gerster et al. | 424/248.53 |
| 4,472,406 A | 9/1984 | Gerster et al. | 424/258 |
| 4,472,407 A | 9/1984 | Stern et al. | 424/258 |
| 4,535,161 A | 8/1985 | Hayakawa | 546/94 |
| 4,552,879 A | 11/1985 | Ishikawa et al. | 514/253 |
| 4,594,347 A | 6/1986 | Ishikawa et al. | 514/252 |
| 4,599,418 A | 7/1986 | Irikura et al. | 544/361 |
| 4,638,067 A | 1/1987 | Culbertson et al. | 546/15 |
| 4,642,355 A | 2/1987 | Nakamura et al. | 548/533 |
| 4,665,079 A | 5/1987 | Culbertson et al. | 514/312 |
| 4,777,175 A | 10/1988 | Culbertson et al. | 514/300 |
| 4,822,801 A | 4/1989 | Domagala et al. | 514/312 |
| 4,874,764 A | 10/1989 | Ueda et al. | 514/254 |
| 4,894,458 A | 1/1990 | Masuzawa et al. | 546/156 |
| 4,935,420 A | 6/1990 | Ueda et al. | 514/235.2 |
| 5,051,509 A | 9/1991 | Nagano et al. | 546/156 |
| 5,097,032 A | 3/1992 | Domagala et al. | 546/156 |
| 5,185,337 A | 2/1993 | Fujii et al. | 514/254 |
| 5,200,558 A * | 4/1993 | Kwan | 562/496 |
| 5,607,942 A | 3/1997 | Petersen et al. | 546/200 |
| 5,639,886 A | 6/1997 | Zerbes et al. | 546/155 |

(List continued on next page.)

FOREIGN PATENT DOCUMENTS

| | | |
|---|---|---|
| EP | 0230295 | 7/1987 |
| EP | 0241206 | 10/1987 |
| EP | 0287951 | 10/1988 |

(List continued on next page.)

OTHER PUBLICATIONS

Berge SM et al. Journal of Pharmaceutical Sciences. 66 (1), pp. 1–19 (1977).*

(List continued on next page.)

*Primary Examiner*—Evelyn Mei Huang
(74) *Attorney, Agent, or Firm*—Ladas & Parry

(57) ABSTRACT

The invention relates to the new arginine salt forms of RS-(±)-9-fluoro-6,7-dihydro-8-(4-hydroxypiperidin-1-yl)-5-methyl-1-oxo-1H,5H-benzo[i,j]quinolizine-2-carboxylic acid, S-(−)-9-fluoro-6,7-dihydro-8-(4-hydroxypiperidin-1-yl)-5-methyl-1-oxo-1H,5H-benzo[i,j]quinolizine-2-carboxylic acid, R-(+)-9-fluoro-6,7-dihydro-8-(4-hydroxypiperidin-1-yl)-5-methyl-1-oxo-1H,5H-benzo[i,j]quinolizine-2-carboxylic acid, a process for their preparation and pharmaceutical formulations which comprise those arginine salt forms as the active ingredient for its use in treating microbial infections.

11 Claims, 3 Drawing Sheets

U.S. PATENT DOCUMENTS

| | | | |
|---|---|---|---|
| 5,677,316 A | 10/1997 | Ao et al. | 514/312 |
| 5,859,026 A | 1/1999 | Ito et al. | 514/312 |
| 5,869,661 A | 2/1999 | Ochi et al. | 544/128 |
| 5,889,009 A | 3/1999 | Miyake et al. | 514/254 |
| 6,034,100 A | 3/2000 | Adachi et al. | 514/312 |
| 6,121,285 A | 9/2000 | Takemura et al. | 514/312 |
| 6,184,388 B1 | 2/2001 | Takemura et al. | 548/566 |
| 6,329,391 B1 | 12/2001 | Ledoussal et al. | 514/312 |
| 2002/0061908 A1 * | 5/2002 | de Souza et al. | 514/294 |

FOREIGN PATENT DOCUMENTS

| | | | |
|---|---|---|---|
| EP | 0304087 | 2/1989 | |
| EP | 0342675 | 11/1989 | |
| EP | 0394553 | 10/1990 | |
| EP | 0541086 | 5/1993 | |
| EP | 0572259 | 12/1993 | |
| EP | 0908181 | 4/1999 | |
| EP | 0919553 | 6/1999 | |
| JP | 57081486 | 5/1982 | |
| JP | 57176987 | 10/1982 | |
| JP | 58090511 | 5/1983 | |
| JP | 63192753 | 8/1988 | |
| JP | 02131483 | 5/1990 | |
| JP | 02188570 | 7/1990 | |
| JP | 02188589 | 7/1990 | |
| JP | 05339238 | 12/1993 | |
| WO | 9420105 | 9/1994 | |
| WO | 9731000 | 8/1997 | |
| WO | 9744034 | 11/1997 | |
| WO | 9914214 | 3/1999 | |
| WO | 9926940 | 6/1999 | |
| WO | 0018404 | 4/2000 | |
| WO | 0068229 | 11/2000 | |
| WO | WO 200068229 A2 * | 11/2000 | A61K/31/4745 |
| WO | 0185095 | 11/2001 | |
| WO | 0185728 | 11/2001 | |
| WO | WO 200185095 A2 * | 11/2001 | A61K/00/00 |
| WO | 0209758 | 2/2002 | |

OTHER PUBLICATIONS

Morita S et al. Tetrahedron Asymmetry, 6(1): pp. 245–254 (1995).*
Kido M et al. Chem. Pharm. Bull 42(4), pp. 872–876 (1994).*
Hashimoto K et al., Chem. Pharm. Bull 44(4), pp. 642–645 (1996).*
Mergler et al. Proceedings of the 12$^{th}$ American Peptide Symposium. Reference cited on p. 2 of EPA 0953577.
Asina, et al., *Tetrahedron Letters*, v38, n5, (1997) 883–886.
Edwards et al. *J. Med. Chem.*, v37, n22 (1994) 3749–3757.
Oizumi et al. *J. Infec. Chemotherapy*, v7 (2001) 191–194.
Haustein et al. *J. of Dermatological Treatment*, v8 (1997) 87–92.
Bundgaard, H. *Design of Prodrugs*. (1985) pp. 1–3.
Hashimoto et al. *Chem. Pharm. Bull.* V44, n4 (1996) pp. 642–645.
Irish, D. et al. *J. of Hospital Infection*, v39 (1998) pp. 19–26.
Kido, M. et al. *Chem. Pharm. Bull.* V42, n4 (1994) pp. 872–876.
Sloan et al. *Physics and Chemistry of the Organic Solid State*, eds. D. Fox, Labes and Weissberer, Interscience Publishers, (1963) 179–182.
Takahashi et al., *Arzheim–Forsc/Drug Res.*, 45(1), Nr.2 (1995), 199–197.
Morita, S. et al. *Tetrahedron Assymetry*, v6, n1 (1995) pp. 245–254.
Morita, S. et al. *Chem. Pharm. Bull.*, 38(7) (1990) 2027–2029.
Ishikawa et al. *Chem. Pharm. Bull.*, 37(8) (1989) 2103–2108.
English translation of Yamada, H. et al. *Iyahukin Kenkyu*, v31, n8 (2000) pp. 519–524.
English translation of Yamada, H. et al. *Iyahukin Kenkyu*, v31, n8 (2000) pp. 525–528.
Berge et al. *J. of Pharmaceutical Sciences*, 66(1) (1977) 1–19.
Abstract of Koike, M. et al., *Iyakuhin Kenkyu*, v21, n5 (1990) pp. 998–1021.
Abstract of Koike, M. et al. *Iyakuhin Kenkyu*, v21, n5 (1990) pp. 1022–1033.
Abstract of Fujita, S. et al. *Iyakuhin Kenkyu*, v21, n6 (1990) pp. 1156–1176.
Abstract of Koike, M. et al. *Yakubutsu Dotai*, v5, n2 (1990) pp. 199–208.
Abstract of Yasuo, A. et al. *Yakuri to Chiryo*, v18, n4 (1990) pp. 1717–1730.
Abstract of Hayakawa, R. et al. *Hifu*, v32, n2 (1990) pp. 217–230.
Abstract of Asada, Y. et al. *Yakuri to Chiryo*, v18, n4 (1990) pp. 1717–1730.
Abstract of Awogi, T. et al. *Iyakuhin Kenkyu*, v21, n4 (1990) pp. 626–635.
Abstract of Matsuzawa, A. et al. *Iyakuhin Kenkyu*, v21, n4 (1990) pp.636–646.
Abstract of Nagao T. et al. *Iyakuhin Kenkyu*, v21, 4 (1990) pp. 647–662.
Abstract of Matsuzawa, A. et al. *Iyahukin Kenkyu*, v21, n4 (1990) pp. 633–670.
Abstract of Hashimoto, K. et al. *Iyahukin Kenkyu*, v21, n4 (1990) pp. 670–677.
Abstract of Furukawa, M. et al. *Iyahukin Kenkyu*, v21, n5 (1990) pp. 989–997.
Abstract of Kojima, K. et al. *Iyakuhin Kenkyu*, v21, n5 (1990) pp. 1034–1052.
Abstract of Nakagiri, N. et al. *Iyakuhin Kenkyu*, v21, n6 (1990) pp. 1144–1155.
Abstract of Aoki, M. et al. *Iyakuhin Kenkyu*, v21, n6 (1990) pp. 1177–1202.
Abstract of Matsuzawa, A. et al. *Iyahukin Kenkyu*, v22, n1 (1990) pp. 61–76.
Abstract of Kurokawa I. et al. *J. Am. Acad. Dermatol.*, v25, n4 (1991) pp. 674–681.
Abstract of Bojar, R. et al. *J. of Investigative Dermatology*, v103, n3 (1994) p. 405.
Abstract of Haustein, U.F. et al. *J. of Dermatological Treatment*, v8, n2 (1997) pp. 87–92.
Abstract of Smith, C. M. et al. *J. of Investigative Dermatology*, v108, n3 (1997) p. 123.
Abstract of Hayakawa, R. et al. *Hifu*, v40, n2 (1998) pp. 165–171.
Fujio, N. et al. *Yakuri to Chiryo*, v26, n7 (1998) pp. 1119–1132.
Kido, M. et al. *Chem. Pharm. Bull.*, v44, n2 (1996) pp. 421–423.
Miller, M.A. et al. *Infection Control and Hospital Epidemiology*, v17, n12 (1995) pp. 811–813.
Nishijima, S. et al. *The Journal of Int'l Medical Research*, v23, (1995) pp. 328–334.
Nishijima, S. et al. *Journal of Dermatology*, v22, (1995) pp. 153–155.

Nishijima, S. et al. *The Journal of Int'l Medical Research*, v24, (1996) pp. 12–16.
Nishijima, S. et al. *Journal of Dermatology*, v21, (1994) pp. 233–238.
Udo, E. E. et al. *J. of Hospital Infection*, v26, (1994) pp. 157–165.
Abstract of Kurokawa, I. et al. *European J. of Dermatology*, v9, n1 (1999) pp. 25–28.
Abstract of Komagata, et al. *Japanese Journal of Antibiotics*, v51, n2 (1998) pp. 130–136.
Abstract of Gollnick, H. et al. *Dermatology*, v196, n1(1998) pp. 119–125.
Abstract of Nishijima, S. et al. *J. of Int'l Medical Research*, v25, n4 (1997) pp. 210–213.
Abstract of Nishijima, S. et al. *J. of In'tl Medical Research*, v24, n6 (1996) pp. 473–477.
Abstract of Akamatsu, H. et al. *J. of Int'l Medical Research*, v23, n1 (1995) pp. 19–26.
Abstract of Takahashi, N. et al. *Arzneimittel–Forschung*, v45, n2 (1995) p. 195.
Abstract of Takahashi, N. et al. *Arzneimittal–Forschung*, v44, n11 (1994) 1pp. 265–1268.
Abstract of Patel, M.V. 39$^{th}$ ICAAC at San Diego Poster No. F0558 (Sep. 26–29, 1999).
Chemical Abstract Doc. No. 123:334723 Vogt, K. et al. *Drugs*, v49, Suppl. 2 (1995).
Chemical Abstracts Doc. No. 123:334716 Nishijima et al. *Drugs*, v49, Suppl. 2 (1995).
Chemical Abstracts Doc. No. 124:21098 Bojar, R.A. et al. *Drugs*, v49, Suppl. 2 (1995).
Chemical Abstracts Doc. No. 122:213914, *Tetrahedon: Asymmetry*, v6, No. 1 (1995).
Chemical Abstracts: Doc. No. 119:4810 Vogt, K. et al. *Eur. J. Clin. Microbiol. Infect.*
Chemical Abstracts: Doc. No. 113:2131188 Morita, S. et al. *Chem. Pharm. Bull.* v38, n7.
Chemical Abstracts: Doc. No. 112:229223, Muto, N. et al. *J. Immunoassay*, v11 n1.
Chemical Abstract: Doc. No. 112: 191305, Koike, M. et al. *J. Chromatogr.* v526, n1.
Chemical Abstract: Doc. No. 112: 178631, Ishikawa, H. et al. *Chem. Pharm. Bull.* v37.
Chemical Abstract: Doc. No. 112:52083, *Chemotherapy*, v37, n9 (1989) pp. 1160–1178.
Abstract of Iwahara, K. et al. *European J. of Dermatology*, v9, n4 (1999) pp. 276–277.
Abstract of Radl, S. et al. *Archiv der Pharmazie*, v329, n3 (1996) pp. 115–119.
Abstract of Andriole, V.T., *Drugs*, v46, Suppl. 3 (1993) pp. 1–7.
Ball, Peter. "The Quinolones: History and Overview", Chapter 1, *The Quinolones*, Second Ed. Academic Press, 1998. pp. 1–28.
Domagala, John M. *Journal of Antimicrobial Chemotherapy* (1994) 33, 685–706.
Suto, Mark J. et al. *J. of Med. Chem.* (1992) 35, 4745–4750.
Abstract of Yamakawa, T. et al. *J. Antimicrobial Chemotherapy*, 49(3) Mar. 2002, 455–465.
Hooper, David C. *Drug Resistance Updates* (1999) 2, 38–55.
Ince, Dilek and David C. Hooper. *Antimicrobial Agents and Chemotherapy* (Oct. 2001) 45(10), 2755–2764.
Fournier, Benedicte and David C. Hooper. *Antimicrobial Agents and Chemotherapy*, (Jan. 1998) 42(1) 121–128.
Zhao, Xilin et al. *Antimicrobial Agents and Chemotherapy*, (Apr. 1998) 42(4) pp. 956–958.
Breines, David M. et al. *Antimicrobial Agents and Chemotherapy*, (Jan. 1997) 41(1) 175–179.
Fournier, Benedicte, et al. *Journal of Bacteriology*, (Feb. 2000) 182(3) 664–671.
Mandell, Lionel et al. *CIP* (2001) 32, Suppl 1, S72–S79.
Gootz, Thomas D. and Katherine E. Brighty. "Chemistry and Mechanism of Action of the Quinolone Antobacterials", The Quinolones, Second Ed. Chap 2. Academic.
Takenouchi, Takashi et al. *Antomicrobial Agents and Chemotherapy*, (Aug. 1996) 40(8) pp. 1835–1842.
Zhao, Xilin, et al. *Proc. Natl. Acad. Sci. USA*, (Dec. 1997) vol. 94, pp. 13991–13996.
Takei, Masaya et al. *Antimicrobial Agents and Chemotherapy*, (Dec. 2001), 45(12), pp. 3544–3547.
Ince, Dilek et al. *Antimicrobial Agents and Chemotherapy*, (Dec. 2000), 44(12) pp. 3344–3350.
Oizumi, Nbuyuki et al. *J. Infect. Chemother.*, (2001) 7: 191–194.

* cited by examiner

CRYSTALLINE FLUOROQUINOLONE ARGININE SALT FORM

FIELD OF THE INVENTION

The present invention relates to a new crystalline form of a fluoroquinolone, viz. arginine salt form thereof, a novel process for manufacturing the novel arginine salt form of the fluoroquinolone, the use of the novel form of the arginine salt of the fluoroquinolone in the manufacture of pharmaceutical formulations and the use of the novel form of the arginine salt of the fluoroquinolone in medicine. More particularly, it relates to the arginine salt form of the chiral fluoroquinolone S-(−)-9-fluoro-6,7-dihydro-8-(4-hydroxypiperidin-1-yl)-5-methyl-1-oxo-1H,5H-benzo[i,j]quinolizine-2-carboxylic acid, a process for preparing the same and its use in pharmaceutical formulations and medicine.

BACKGROUND OF THE INVENTION

The chiral fluoroquinolone known under the name S-(−)-9-fluoro-6,7-dihydro-8-(4-hydroxypiperidin-1-yl)-5-methyl-1-oxo-1H,5H-benzo[i,j]quinolizine-2-carboxylic acid is described in JP Patent 63,192,753A, JP Patent 05,339,238A, and in our pending U.S. patent applications Ser. Nos. 09/566,875, 09/640,947 and 09/802,793 and WO 00/68229, PCT Application Nos. PCT/IN00/00111 and PCT/IN01/00097.

S-(−)-9-fluoro-6,7-dihydro-8-(4-hydroxypiperidin-1-yl)-5-methyl-1-oxo-1H,5H-benzo[i,j]quinolizine-2-carboxylic acid is an optically active isomer of the racemic compound which is claimed in U.S. Pat. No. 4,399,134.

S-(−)-9-fluoro-6,7-dihydro-8-(4-hydroxypiperidin-1-yl)-5-methyl-1-oxo-1H,5H-benzo[i,j]quinolizine-2-carboxylic acid has an aqueous solubility of 0.8–2.0 mg/ml over the pH range 8.0–9.5 at 28° C., thus creating problems in having to formulate the drug as a tablet or capsule, or in making formulations for gavage and parenteral injection. The need for a salt is clearly indicated, as the lack of an appropriate salt form can hinder the development of dosage forms acceptable for systemic use in mammals.

S-(−)-9-fluoro-6,7-dihydro-8-(4-hydroxypiperidin-1-yl)-5-methyl-1-oxo-1H,5H-benzo[i,j]quinolizine-2-carboxylic acid has a pKa value of 6.80 suggesting a weak acid character and thus an ability to form a salt with an appropriate base. Generally, conversion of a pharmacologically active compound into a salt form induces a change in the compound's physicochemical properties such as solubility, absorption velocity, etc.

Pharmaceutically more desirable salt forms may be selected by studying whether or not a crystalline or amorphous form, or polymorph or pseudopolymorph can be produced, and determining the properties including its physicochemical or biological properties. A pseudopolymorph is a polymorph that differs from a true polymorph by the incorporation of solvent (Solid-state Chemistry of Drugs, $2^{nd}$ Ed. S. R. Byrn et al (Eds). SSCI, Inc. 1999, p-514).

Pharmaceutically acceptable salts of racemic 9-fluoro-6,7-dihydro-8-(4-hydroxypiperidin-1-yl)-5-methyl-1-oxo-1H,5H-benzo[i,j]quinolizine-2-carboxylic acid such as salts with inorganic bases and organic bases are mentioned in the text of Otsuka's U.S. Pat. No. 4,399,134. Besides salts with inorganic bases and organic bases, amino acid salts of S-(−)-9-fluoro-6,7-dihydro-8-(4-hydroxypiperidin-1-yl)-5-methyl-1-oxo-1H,5H-benzo[i,j]quinolizine-2-carboxylic acid are identified in our pending U.S. patent applications Ser. No. 09/566,875 and U.S. patent application Ser. No. 09/640,947, WO 00/68229 and PCT Application No. PCT/IN00/00111. Arginine salt forms of S-(−)-9-fluoro-6,7-dihydro-8-(4-hydroxypiperidin-1-yl)-5-methyl-1-oxo-1H,5H-benzo[i,j]quinolizine-2-carboxylic acid are identified in our pending U.S. patent application Ser. No. 09/802,793 and PCT Application No. PCT/IN01/00097. The subject matter of these applications is incorporated herein by reference. To date, no literature reference teaches about the amino acid salts of RS-(+/−)-9-fluoro-6,7-dihydro-8-(4-hydroxypiperidin-1-yl)-5-methyl-1-oxo-1H,5H-benzo[i,j]quinolizine-2-carboxylic acid or R-(+)-9-fluoro-6,7-dihydro-8-(4-hydroxypiperidin-1-yl)-5-methyl-1-oxo-1H,5H-benzo[i,j]quinolizine-2-carboxylic acid.

S-(−)-9-fluoro-6,7-dihydro-8-(4-hydroxypiperidin-1-yl)-5-methyl-1-oxo-1H,5H-benzo[i,j]quinolizine-2-carboxylic acid, L-arginine salt 0.25 hydrate and S-(−)-9-fluoro-6,7-dihydro-8-(4-hydroxypiperin-1-yl)-5-methyl-1-oxo-1H,5H-benzo[i,j]quinolizine-2-carboxylic acid, L-arginine salt, 0.75 hydrate described in Examples 7 and 8 of U.S. patent applications Ser. Nos. 09/566,875 and 09/640,947, WO 00/68229 and PCT Application No. PCT/IN00/00111 respectively are highly hygroscopic and turn into syrups on exposure at a relative humidity of 41%. Additionally, arginine salt forms described in our pending U.S. patent application Ser. No. 09/802,793 and PCT Application No. PCT/IN01/00097 are either amorphous or only partially crystalline and are to a certain degree hygroscopic. Many hydrates and salts associated with water are susceptible to changes in humidity, are hygroscopic under adverse storage conditions and during pharmaceutical processing of them to medicament forms.

The amino acid salts, inorganic base and alkali salts and organic base salts and specially the arginine salt forms of S-(−)-9-fluoro-6,7-dihydro-8-(4-hydroxypiperidin-1-yl)-5-methyl-1-oxo-1H,5H-benzo[i,j]quinolizine-2-carboxylic acid were prepared and studied by the inventors and it was found that:

(a) an arginine salt may exist in a crystalline form having distinctive physicochemical, solubility and stability properties;

(b) the crystalline arginine salt is less prone than the sodium salt to absorb moisture at specified humidity levels;

(c) the crystalline arginine salt, possesses a lower propensity to cause phlebitis than the sodium and potassium salts as determined in rats by intravenous administration; and (d) the crystalline arginine salt is less toxic in rodents than the alkali salt forms.

In summary, the crystalline form of the arginine salt of S-(−)-9-fluoro-6,7-dihydro-8-(4-hydroxypiperidin-1-yl)-5-methyl-1-oxo-1H,5H-benzo[i,j]quinolizine-2-carboxylic acid has been found by the inventors to have very desirable properties in possessing under specified conditions, less hygroscopicity, favourable aqueous solubility, a low propensity to cause phlebitis, and favourable acute toxicity values. This form is expected to be very useful as a pharmaceutical agent as compared with the previously described arginine salt forms, sodium salt, other inorganic base/alkali salts, organic base salts and other amino acid salts. These advantages will be apparent from the experimental data shown hereafter.

SUMMARY OF THE INVENTION

New arginine salts of RS-(±)-9-fluoro-6,7-dihydro-8-(4-hydroxypiperidin-1-yl)-5-methyl-1-oxo-1H,5H-benzo[i,j]

quinolizine-2-carboxylic acid, R-(+)-9-fluoro-6,7-dihydro-8-(4-hydroxypiperidin-1-yl)-5-methyl-1-oxo-1H,5H-benzo[i,j]quinolizine-2-carboxylic acid and S-(−)-9-fluoro-6,7-dihydro-8-(4-hydroxypiperidin-1-yl)-5-methyl-1-oxo-1H,5H-benzo[i,j]quinolizine-2-carboxylic acid are described. Compositions comprising one or more of these salts and methods for preparing the salts are described. The use of the salts in medicine is also described.

More particularly, a new L-arginine salt form of S-(−)-9-fluoro-6,7-dihydro-8-(4-hydroxypiperidin-1-yl)-5-methyl-1-oxo-1H,5H-benzo[i,j]quinolizine-2-carboxylic acid of the formula I

DISCLOSURE OF THE INVENTION

The main objective of the invention accordingly relates to new DL arginine salts and D-arginine salts and L-arginine salts of of RS-(±)-9-fluoro-6,7-dihydro-8-(4-hydroxypiperidin-1-yl)-5-methyl-1-oxo-1H,5H-benzo[i,j]quinolizine-2-carboxylic acid, R-(+)-9-fluoro-6,7-dihydro-8-(4-hydroxypiperidin-1-yl)-5-methyl-1-oxo-1H,5H-benzo[i,j]quinolizine-2-carboxylic acid and S-(−)-9-fluoro-6,7-dihydro-8-(4-hydroxypiperidin-1-yl)-5-methyl-1-oxo-1H,5H-benzo[i,j]quinolizine-2-carboxylic acid.

Where particular stereoisomeric forms are described in this invention, they are meant to be substantially free of any Formula I

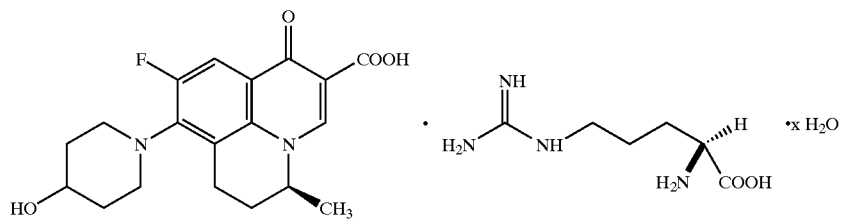

is described in which x denotes 0, 0.25, 0.5, 0.75, 1.0, 2.0 or 3.0. The novel crystalline form of the L-arginine salt of S-(−)-9-fluoro-6,7-dihydro-8-(4-hydroxypiperidin-1-yl)-5-methyl-1-oxo-1H,5H-benzo[i,j]quinolizine-2-carboxylic acid can be used in full scale manufacturing of pharmaceutical formulations.

Antibacterial compositions comprising the S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt form as an active component are described.

BRIEF DESCRIPTION OF THE DRAWINGS

The invention will now be described in further detail with reference to the accompanying drawings.

other stereoisomeric configuration. Substantially free should be taken to mean that the active ingredient contains at least 90% by weight of the desired stereoisomer and 10% by weight or less of other stereoisomers. Preferably the weight % ratio is better than 95:5 and most preferably 99:1 or better. For example, S-(−)-9-fluoro-6,7-dihydro-8-(4-hydroxypiperidin-1-yl)-5-methyl-1-oxo-1H,5H-benzo[i,j]quinolizine-2-carboxylic acid L-arginine contains at least 90% by weight of this stereoisomer and 10% by weight or less of other configurations of 9-fluoro-6,7-dihydro-8-(4-hydroxypiperidin-1-yl)-5-methyl-1-oxo-1H,5H-benzo[i,j]quinolizine-2-carboxylic acid L-arginine.

The invention relates to new crystalline arginine salts of S-(−)-9-fluoro-6,7-dihydro-8-(4-hydroxypiperidin-1-yl)-5-methyl-1-oxo-1H,5H-benzo[i,j]quinolizine-2-carboxylic acid, wherein the arginine component may be L-arginine, D-arginine or DL-arginine.

More particularly, the invention relates to a new crystalline L-arginine salt of S-(−)-9-fluoro-6,7-dihydro-8-(4-hydroxypiperidin-1-yl)-5-methyl-1-oxo-1H,5H-benzo[i,j]quinolizine-2-carboxylic acid of the formula I Formula I

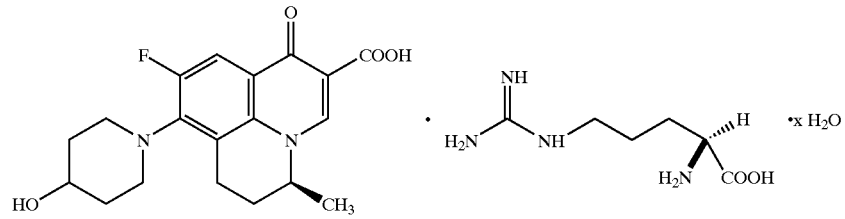

in which x denotes 0, 0.25, 0.5, 0.75, 1.0, 2.0 or 3.0. Preferably, the L-arginine crystalline salt is a monohydrate.

The salt of Formula I has favourable aqueous solubility, is stable in humid conditions, has favorable bioavailability, has a lower propensity to cause phlebitis and lower toxicity when administered in mammals.

This invention also relates to a process for the preparation of the salt of Formula I, to its use in pharmaceutical compositions and in medicine.

The arginine isomer used can be a racemic mixture of the chiral isomers or the R-isomer or the S-isomer. A preferred arginine isomer is the S-isomer, that is L-arginine.

Figure 1:
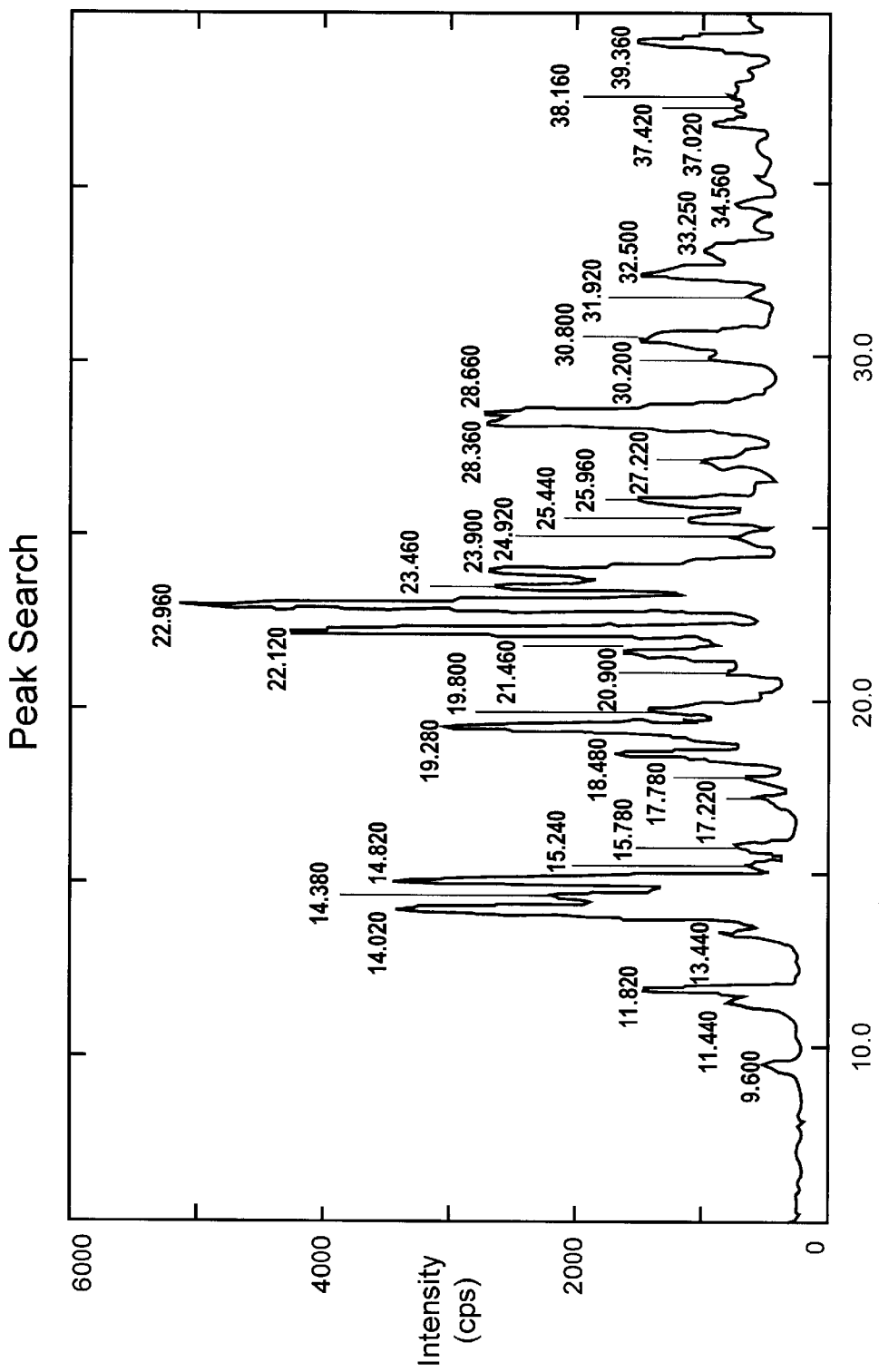
FIG. 1 represents the X-Ray Powder Diffraction (XRPD) spectrum of the crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt of the invention.

The arginine salt of the invention is described as crystalline because of the high degree of crystallinity of the form as depicted by the XRD spectrum provided in FIG. 1. The form is shown to have distinct physicochemical properties, is more stable to decomposition from uptake of moisture at specified conditions, is distinguished by increased stability, in particular during storage at specified humidities and can be dried without caking or decomposing at elevated temperatures under reduced pressure. This form is particularly suitable for the preparation of stable pharmaceutical preparations, and has favourable biological properties.

This form, while less hygroscopic than the compounds of Examples 7 and 8 of U.S. patent application Ser. Nos. 09/566,875 and 09/640,947, WO 00/68229 and PCT Application No. PCT/IN00/00111, is to a certain degree hygroscopic. In stability studies at varying relative humidity conditions, this form was found to remain stable at relative humidity values of 22% at 25° C. In stability studies at elevated temperatures, this form remained stable with no decomposition up to 100° C., however, there was reduction in levels of water content and solvent content. On drying the forms at elevated temperatures up to 100° C. over different periods of time and under different humidity conditions, the amounts of water found associated with the salt are altered. However, there is no change in the XRD-spectrum of the form. Without being bound to any theory, from this the inventors infer that the amount of water associated with the preferred form of the invention is not superficial and the preferred form of the invention is substantially a monohydrate.

Hydrates are said to exist when the drug substance incorporates water in the crystal lattice in either stochiometric or non-stochiomnetric amounts" (Stephen Byrn, et. al., Pharmaceutical Solids: A strategic Approach to Regulatory Considerations, Pharma. Res. Vol. 12 (7), 1995, 945–954).

The inventors have found that S-(−)-9-fluoro-6,7-dihydro-8-(4-hydroxypiperidin-1-yl)-5-methyl-1-oxo-1H,5H-benzo[i,j]quinolizine-2-carboxylic acid arginine salt form of this invention, has acceptable aqueous solubility of 1 mg/ml extending to 30 mg/ml, over the pH range 7.0–9.5 at ambient temperatures. The solubility of this crystalline form is 30 mg/ml at pH 9.5. The L-arginine salt form is stable on heating at temperatures up to 100° C. at relative humidity ranges up to 22%. This form has an acceptable dissolution rate.

The combination of physical properties of the novel S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt form of the present invention with respect to the degree of crystallinity, particle diameter, density, hygroscopicity, water content and content of other solvents is favourable and permits the manufacturing of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt in a composition which possesses the desired properties.

The properties of this crystalline form including the melting point is of a value that endow the form with desirable compression and flow properties for the processing of dosage forms useful for medicinal purposes.

This crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid arginine salt also has desirable physicochemical properties as hereinbefore mentioned, and is characterised by parameters such as XRD, DSC, particle size and powder density.

Figure 2:
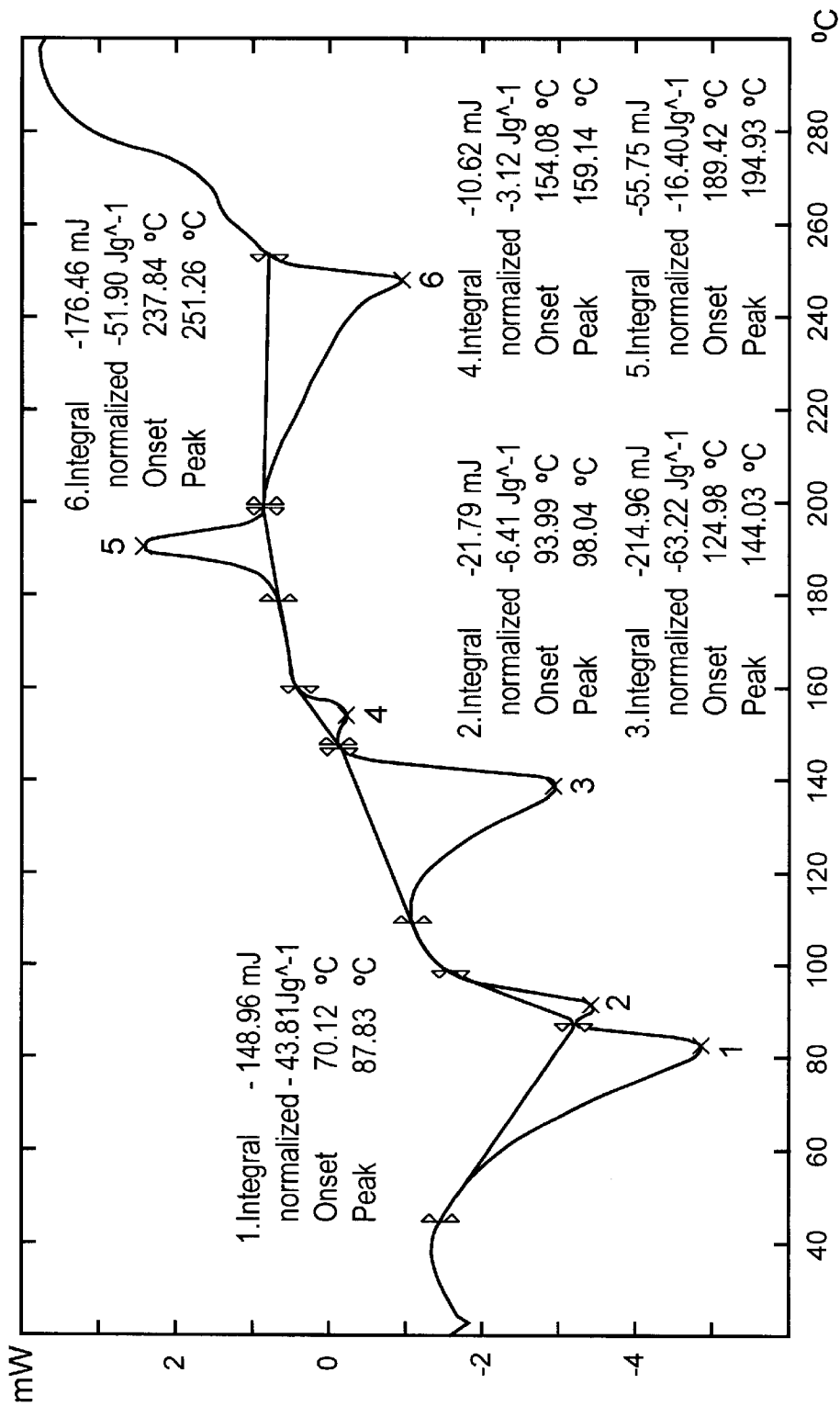
FIG. 2 represents the Differential Scanning Calorimeter (DSC) thermogram of the crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt of the invention.

The more crystalline form is described below:
(a) The degree of crystallinity as determined by X-ray powder diffraction is shown in FIG. 1, X-ray powder diffraction (2θ): 14.02±0.2, 14.82±0.2, 19.28±0.2, 22.12±0.2, 22.96±0.2, 23.46±0.2, 28.36±0.2.
(b) A thermogram as determined by Differential Scanning Calorimetry has shown an exotherm at 194.93° C. (onset at 189.42° C.) and one endotherm at 251.26° C. as shown in FIG. 2. Other endotherms at 87.83° C., 98.04° C., 144.03° C. and 159.14° C. are also observable, which endotherm readings may slightly fluctuate in different samples.

Figure 3:
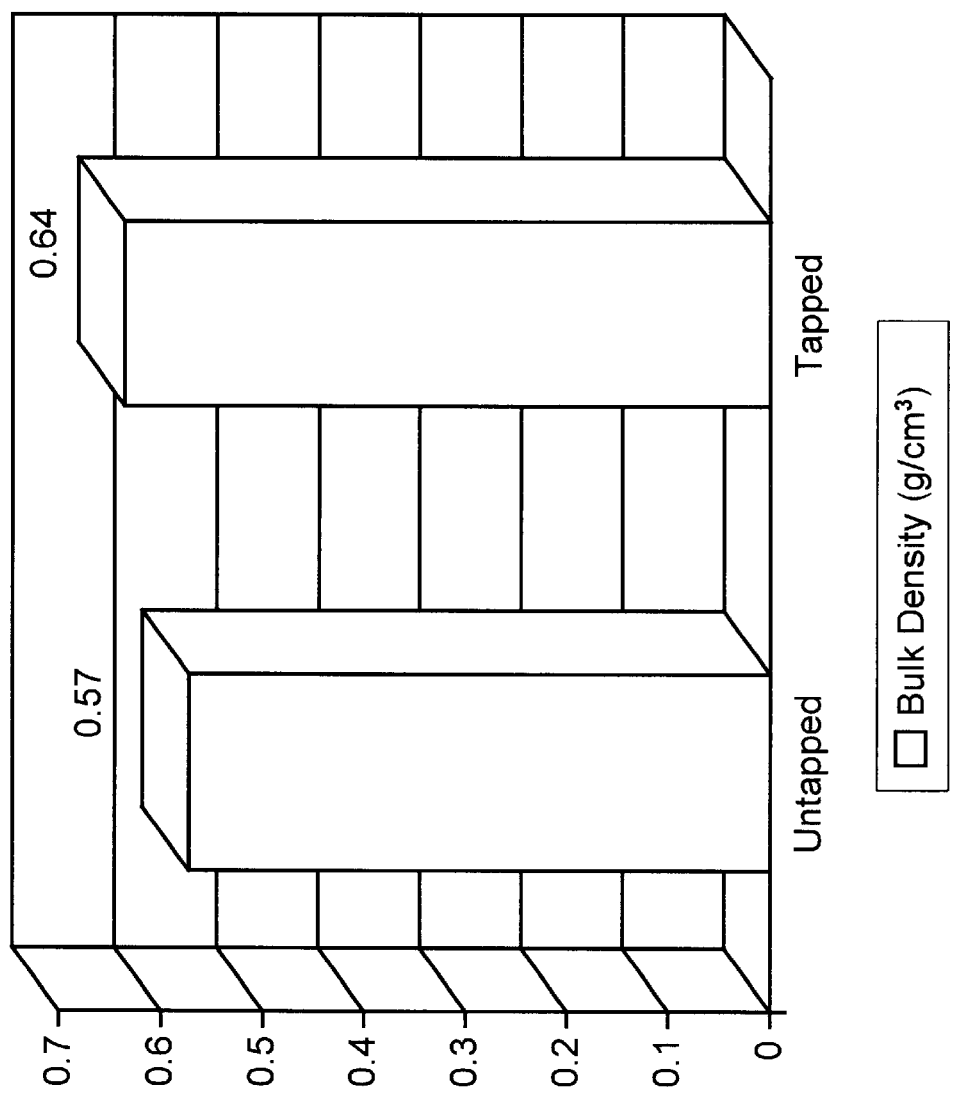
FIG. 3 shows that the bulk density of the crystalline form of the invention S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt is between 0.57 g/cm$^3$ (untapped) and 0.64 g/cm$^3$ (tapped).

It is desirable that the crystalline form also has the following properties:
(c) Particle size measured as mean mass diameter (MMD) as determined by laser diffraction technique is less than or equal to 40 μm, preferably the mean mass diameter is 32.00 μm±8 μm as determined by laser diffraction technique, and as shown in Table 1;
(d) Density between 0.57 g/cm$^3$ (untapped) and 0.64 g/cm$^3$ (tapped) as shown in FIG. 3. Untapped density is defined as 25 gm/untapped volume. The results are provided in FIG. 3. Tapped density is defined as 25 gm/tapped volume. The results are provided in FIG. 3.
(e) Hygroscopicity not exceeding 3% increase of weight upon storage for 14 days up to 22% relative atmospheric humidity at 30° C. as determined gravimetrically, but with full retention of flow properties;
(f) A content of water between 4.0% to 4.4% by weight as determined by titration according to Karl Fischer.
(g) The content of the organic solvent is less than 0.05% by weight as determined by gas chromatography. When acetone is used as solvent in the preparation of this form, the content of acetone is less than 0.3%, preferably less than 0.2% by weight as determined by gas chromatography. When acetonitrile is used as solvent in the preparation of this form, the content of acetonitrile is less than 0.04%, preferably less than 0.03% by weight as determined by gas chromatography.
(h) The solubility in a solution of pH 9.5 is 30.0 mg/ml.

The S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt of this invention exhibits the same antibacterial minimum inhibitory concentration (MIC) values as the free active ingredient, S-(−)-9-fluoro-6,7-dihydro-8-(4-hydroxypiperidin-1-yl)-5-methyl-1-oxo-1H, 5H-benzo[i,j]quinolizine-2-carboxylic acid.

The crystalline form of S-(−)-9-fluoro-6,7-dihydro-8-(4-hydroxypiperidin-1-yl)-5-methyl-1-oxo-1H,5H-benzo[i,j]-quinolizine-2-carboxylic acid L-arginine salt has antimicrobial activity:

It has potent activity against resistant *Staphylococcus aureus*.

It has ability to resist drug efflux in Gram-positive organisms.

It has the unusual ability to retain potency at an acidic pH of 5.5.

It is effective in treating respiratory pathogens.

It is effective in treating resistant mutants.

It has superior cidal action against slow-growing Staphylococci.

It scores over the standard drugs in terms of eradication efficacy for Staphylococci from vital organs and thigh muscle.

It exhibits unusual superior cidal effect even with a high density bacterial inoculum ($10^8$ cfu/ml); a standard recommended inoculum is $10^6$ cfu/ml.

S-(−)-9-fluoro-6,7-dihydro-8-(4-hydroxypiperidin-1-yl)-5-methyl-1-oxo-1H,5H-benzo[i,j]-quinolizine-2-carboxylic acid D-arginine salt, S-(−)-9-fluoro-6,7-dihydro-8-(4-hydroxypiperidin-1-yl)-5-methyl-1-oxo-1H,5H-benzo[i,j]-quinolizine-2-carboxylic acid DL-arginine salt, R-(+)-9-fluoro-6,7-dihydro-8-(4-hydroxypiperidin-1-yl)-5-methyl-1-oxo-1H,5H-benzo[i,j]-quinolizine-2-carboxylic acid L-arginine salt, R-(+)-9-fluoro-6,7-dihydro-8-(4-hydroxypiperidin-1-yl)-5-methyl-1-oxo-1H,5H-benzo[i,j] quinolizine-2-carboxylic acid D-arginine salt, R-(+)-9-fluoro-6,7-dihydro-8-(4-hydroxypiperidin-1-yl)-5-methyl-1-oxo-1H,5H-benzo[i,j]-quinolizine-2-carboxylic acid DL-arginine salt, R, S-9-fluoro-6,7-dihydro-8-(4-hydroxypiperidin-1-yl)-5-methyl-1-oxo-1H,5H-benzo[i,j]-quinolizine-2-carboxylic acid L-arginine salt, R,S-9-fluoro-6,7-dihydro-8-(4-hydroxypiperidin-1-yl)-5-methyl-1-oxo-1H,5H-benzo[i,j]-quinolizine-2-carboxylic acid D-arginine salt and R, S-9-fluoro-6,7-dihydro-8-(4-hydroxypiperidin-1-yl)-5-methyl-1-oxo-1H,5H-benzo[i,j]-quinolizine-2-carboxylic acid DL-arginine salt also have antimicrobial activity. It is to be noted that as S-(−)-9-fluoro-6,7-dihydro-8-(4-hydroxypiperidin-1-yl)-5-methyl-1-oxo-1H,5H-benzo[i,j]-quinolizine-2-carboxylic acid has more potent antimicrobial activity than R-(+)-9-fluoro-6,7-dihydro-8-(4-hydroxypiperidin-1-yl)-5-methyl-1-oxo-1H,5H-benzo[i,j]-quinolizine-2-carboxylic acid and RS-(−)-9-fluoro-6,7-dihydro-8-(4-hydroxypiperidin-1-yl)-5-methyl-1-oxo-1H, 5H-benzo[i,j]-quinolizine-2-carboxylic acid, this same difference in potency will also be displayed by their respective arginine salts.

The present invention also relates to a process for preparing the novel crystalline form of the arginine salt. A process for the manufacture of the crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt comprises the following consecutive steps:

a) dissolving S-(−)-9-fluoro-6,7-dihydro-8-(4-hydroxypiperidin-1-yl)-5-methyl-1-oxo-1H,5H-benzo[i,j]quinolizine-2-carboxylic acid with L-arginine in an organic solvent and water to form a solution;

b) cooling the solution to provide a crystalline substance;

c) isolating the crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt at <35° C. by filtration or centrifugation;

d) purifying and drying the crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt using conventional methods.

The ratio of L-arginine to S-(−)-9-fluoro-6,7-dihydro-8-(4-hydroxypiperidin-1-yl)-5-methyl-1-oxo-1H,5H, benzo[i,j]quinolizine-2-carboxylic acid ranges from 0.93 to 1.49 molar equivalent of L-arginine to 1.0 molar equivalent of S-(−)-9-fluoro-6,7-dihydro-8-(4-hydroxypiperidin-1-yl)-5-methyl-1-oxo-1H,5H, benzo[i,j]quinolizine-2-carboxylic acid. Preferably the molar ratio of L-arginine to S-(−)-9-fluoro-6,7-dihydro-8-(4-hydroxypiperidin-1-yl)-5-methyl-1-oxo-1H,5H, benzo[i,j]quinolizine-2-carboxylic acid is 1.0:1.0 mole.

Preferably the solvents used in step (a) are an organic solvent and water; more preferably the organic solvent is acetone or acetonitrile. The proportion of organic solvent to water ranges from 20% to 80% depending upon the organic solvent used. The proportion of water to organic solvent ranges from 16.6% water to 33.3% water of the total volume of organic solvent and water used. A preferred proportion of water to organic solvent is 20% water of the total volume of water and organic solvent used.

Preferably the solution of step (a) is stirred at a temperature 50 to 60° C. for 45–60 minutes.

Preferably in step (a) the solution is treated with activated charcoal at 50 to 60° C., filtered hot and diluted with an additional amount of organic solvent. In the case when the organic solvent is acetone, the ratio ranges from 0.9 to 1.1 parts by weight of the acid to 2.4 to 2.6 parts by volume of water to 9.0 to 11 parts by volume of acetone, preferably 1 part by weight of acid to 2.5 parts by volume of water to 10 parts by volume of acetone. In the case when the organic solvent is acetonitrile, the ratio ranges from 0.9 to 1.1 parts by weight of the acid to 2.3 to 2.5 parts by volume of water to 11.0 to 13 parts by volume of acetonitrile, preferably 1 part by weight of acid:2.4 parts by volume of water: 12 parts by volume of acetonitrile.

The amount of water used depends on the nature of the organic solvent used. When the organic solvent is acetone, the preferred ratio of water to acetone is 1 part by volume of water to 4 parts by volume of acetone and when acetonitrile is the organic solvent used, the preferred ratio of water to acetonitrile is 1 part by volume of water and 5 parts by volume of acetonitrile. It is also based on the amount of S-(−)-9-fluoro-6,7-dihydro-8-(4-hydroxypiperidin-1-yl)-5-methyl-1-oxo-1H,5H, benzo[i,j]quinolizine-2-carboxylic acid and the nature of the organic solvent used, preferably when 1 part by weight of acid is used, 2.5 parts by volume of water are used and 5 parts to 10 parts by volume of acetone are used. When acetonitrile is the solvent, preferably for 1 part by weight of acid, 2.4 parts by volume of water and 12 parts by volume of acetonitrile are used.

In step (b), the solution is cooled from 0° C. to 40° C., more preferably from 30° C. to 35° C.

Preferably in step (c), a crystalline substance is obtained by filtration.

In a preferred embodiment, L-arginine is added to a suspension or solution of S-(−)-9-fluoro-6,7-dihydro-8-(4-hydroxypiperidin-1-yl)-5-methyl-1-oxo-1H,5H-benzo[i,j]quinolizine-2-carboxylic acid in an organic solvent and water. The organic solvent may be selected from acetone or acetonitrile. The amounts of organic solvent and water used are so manipulated that when the reaction mixture is stirred for 45–60 minutes at 50 to 60° C. a solution is provided, and subsequent cooling from 0° C. to 40° C., preferably to 30–35° C. provides the crystalline salt of the invention. The desired salt is isolated by filtration or centrifugation and washed with additional amount of the respective organic solvent used and dried preferably under reduced pressure and heating up to 65–70° C.

Yet a further aspect of the invention is that the synthesis of optically pure S-(−)-9-fluoro-6,7-dihydro-8-(4-hydroxypiperidin-1-yl)-5-methyl-1-oxo-1H,5H-benzo[i,j]quinolizine-2-carboxylic acid arginine salt is also preferably prepared by enhancement of the optically impure or partially pure S-(−)-9-fluoro-6,7-dihydro-8-(4-hydroxypiperidin-1-yl)-5-methyl-1-oxo-1H,5H-benzo[i,j]quinolizine-2-carboxylic acid using L-arginine, followed by crystallisation of the resulting optically pure salt. A less optically pure S-(−)-9-fluoro-6,7-dihydro-8-(4-hydroxypiperidin-1-yl)-5- methyl-1-oxo-1H,5H-benzo[i,j]quinolizine-2-carboxylic acid used in this process may range from a mixture of 70% of S-(−)-isomer and 30% of R-(+)-isomer to 97% of S-(−)-isomer and 3% of R-(+)-isomer, preferably a mixture of 88% of S-(−)-isomer and 12% of R-(+)-isomer.

A general method for enhancement in optically purity of S-(−)-9-fluoro-6,7-dihydro-8-(4-hydroxypiperidin-1-yl)-5-methyl-1-oxo-1H,5H-benzo[i,j]quinolizine-2-carboxylic acid using L-arginine comprises, (a) suspending a partially optically impure mixture of 9-fluoro-6,7-dihydro-8-(4-hydroxypiperidin-1-yl)-5-methyl-1-oxo-1H,5H-benzo[i,j]quinolizine-2-carboxylic acid comprising 70% S-(−) isomer and 30% R-(+)-isomer to 97% S-(−) isomer and 3% R-(+)-isomer, preferably 88% S-(−) isomer and 12% R-(+)-isomer in water and organic solvent mixture. The ratio of water to organic solvent can be selected from 1.0:1.0 to 1.0:2.0, preferably 1.0:1.18. Organic solvent can be selected from acetone or acetonitrile, preferably acetone. An equimolar quantity of L-arginine is added to the suspension and the suspension is heated at 40 to 70° C., preferably 50 to 60° C. to obtain a clear solution. 2 to 3 times more amount of the organic solvent than originally used is added, preferably 2.4 to 2.5 times more, and the suspension is stirred at 0 to 45° C., preferably 30 to 35° C. for 1 hr to 5 h, preferably 2 hr, to effect the crystallization. The product is isolated by filtration and drying.

Yet a further aspect of the invention is that the synthesis of optically pure S-(−)-9-fluoro-6,7-dihydro-8-(4-hydroxypiperidin-1-yl)-5-methyl-1-oxo-1H,5H-benzo[i,j]quinolizine-2-carboxylic acid arginine salt is also preferably prepared by enhancement of the optically impure or partially pure S-(−)-9-fluoro-6,7-dihydro-8-(4-hydroxypiperidin-1-yl)-5-methyl-1-oxo-1H,5H-benzo[i,j]quinolizine-2-carboxylic acid using D-arginine, followed by crystallisation of the resulting optically pure salt. A less optically pure S-(−)-9-fluoro-6,7-dihydro-8-(4-hydroxypiperidin-1-yl)-5-methyl-1-oxo-1H,5H-benzo[i,j]quinolizine-2-carboxylic acid used in this process may range from a mixture of 70% of S-(−)-isomer and 30% of R-(+)-isomer to 97% of S-(−)-isomer and 3% of R-(+)-isomer, preferably a mixture of 88% of S-(−)-isomer and 12% of R-(+)-isomer.

The process for manufacturing the crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt differs from the earlier known processes in that it can be controlled to give a crystalline polymorphic form of the salt form through use of the respective conditions that are described and shown to provide the result. This process can be carried out in conventional chemical process equipment. Preferably the product that is produced is substantially a monohydrate.

Another aspect of the invention is the preparation of the DL- and D-arginine salt of S-(−)-9-fluoro-6,7-dihydro-8-(4-hydroxypiperidin-1-yl)-5-methyl-1-oxo-1H,5H-benzo[i,j]quinolizine-2-carboxylic acid and of the DL-, D- and L-arginine salts of R(+)-9-fluoro-6,7-dihydro-8-(4-hydroxypiperidin-1-yl)-5-methyl-1-oxo-1H,5H-benzo[i,j]quinolizine-2-carboxylic acid and DL-, D- and L-arginine salt of RS(±)-9-fluoro-6,7-dihydro-8-(4-hydroxypiperidin-1-yl)-5-methyl-1-oxo-1H,5H-benzo[i,j]quinolizine-2-carboxylic acid The process comprises using a suspension of the appropriate enantiomer/racemic mixture of 9-fluoro-6,7-dihydro-8-(4-hydroxypiperidin-1-yl)-5-methyl-1-oxo-1H,5H-benzo[i,j]quinolizine-2-carboxylic acid in a $C_1$–$C_3$ alkanol solvent, preferably methanol, ethanol, isopropanol, adding an aqueous solution of the appropriate enantiomer of arginine in preferably equimolar quantities, stirring the mixture at 40–70° C., preferably 60–65° C. for 10–45 minutes, preferably 15 minutes, evaporating the solution to dryness under reduced pressure to give the desired salt.

S-(−)-9-fluoro-6,7-dihydro-8-(4-hydrbxypiperidin-1-yl)-5-methyl-1-oxo-1H,5H-benzo[i,j]quinolizine-2-carboxylic acid may be prepared by following the procedure described in U.S. Pat. No. 4,399,134. L-arginine salt and D-arginine are commercially available from Ajinomoto, Japan. The cost of naturally occurring L-arginine is considerably cheaper than the enantiomeric D-arginine. One facet of this invention is the description of S-(−)-9-fluoro-6,7-dihydro-8-(4-hydroxypiperidin-1-yl)-5-methyl-1-oxo-1H,5H-benzo[i,j] quinolizine-2-carboxylic acid L-arginine which utilizes the inexpensive naturally occurring and readily available L-arginine for making the crystalline salt of the invention.

A comparison between the novel form of the L-arginine salt prepared by the process of the present invention and those obtained from the experiments disclosed in the prior art shows that the salt of the present invention is substantially a monohydrate, is stable up to 100° C., and at relative humidity up to 22% at 25° C., and has favorable aqueous solubility, all attributes essential to the preparation of pharmaceutical compositions. This novel crystalline form of S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt is stable under typical storage conditions, has good bioavailability in mammals, has lower phlebitis-forming potential on administration to mammals, has low or reduced toxicity, has acceptable disintegration and dissolution rates, and hence is very useful for pharmaceutical manufacturing and for use in medicine. The form is specially suitable for treating diseases caused by microbial infections. The form is suitable for long-term intravenous therapy in critically ill patients or patients in intensive care units. Injectable preparations of the L-arginine salt can be readily prepared in view of its availability in a bulk form that remains stable under specified conditions, its favorable aqueous solubility, its ideal suitability in not causing venous inflammation on repeated intravenous administration, and its safety from adverse toxicity.

S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt form of this invention can be present in pharmaceutical formulations as the only active compound or can be combined with other active ingredients such as other antibacterial agents.

The invention therefore also relates to liquid and solid pharmaceutical formulations which comprise the arginine salt of the invention, such as for example, injectable solutions, suspensions, emulsions, tablets, coated tablets, coated tablet cores, capsules, solutions, troches, dispersions, patches, powders, lotions, gels, sprays, pellets, granules, suppositories, hard or soft gelatin capsules, ointments, creams and the like.

The pharmaceutical formulations are prepared in a manner known per se, for example by mixing, stirring, suspending, dispersing, emulsifying, dissolving and the like, the active compounds with or in the pharmaceutical auxiliaries such as a carrier, diluent, solvent or excipient and processing the components to pharmaceutically suitable forms for parenteral, oral, topical, intranasal, buccal or rectal administration and the like.

Pharmaceutical formulations can be formulated together with auxiliaries and additives usually employed in pharmacy, such as tablet binders, fillers, preservatives, tablet disintegrating agents, flow regulating, agents, plasticizers, wetting agents, dispersing agents, emulsifiers, solvents, pH altering additives, flavourings and the like.

The total daily dose range is generally from about 200 mg to about 1500 mg of the arginine salt form. However, the dose may be higher or lower depending on the needs and conditions of the patient.

The following detailed examples serve to more fully illustrate the invention without limiting its scope.

EXAMPLE 1

Preparation of S-(−)-9-Fluoro-6,7-dihydro-8-(4-hydroxypiperidin-1-yl)-5-methyl-1-oxo-1H,5H-benzo[i,j]quinolizine-2-carboxylic Acid L-Arginine Salt Hydrate S-(−)-9-Fluoro-6,7-dihydro-8-(4-hydroxypiperidin-1-yl)-5-methyl-1-oxo-1H,5H-benzo[i,j]quinolizine-2-carboxylic acid (750 gm, 2.083 mole) was suspended in acetone (2250 ml). To this suspension was added L-arginine (337.5 g, 1.939 mole) and water (1875 ml) under stirring. The mixture was stirred at 55 to 60° C. for one hour to obtain a clear solution. To the solution was added activated carbon (37.5 gm) and the solution was filtered hot. To the filtrate was added acetone (5250 ml). The reaction mixture was stirred for an additional for 2 hours at 30–35° C. then allowed to cool to 5° C. The obtained solid was filtered at suction and washed with acetone. The wet solid was dried in a vacuum oven at 80–85° C. to afford titled compound as a cream coloured powder. Yield 1035 gm. melting point 238–243° C. $[\alpha]_D^{25} = -184.25°$ (c=1, methanol).

EXAMPLE 2

Preparation of S-(−)-9-Fluoro-6,7-dihydro-8-(4-hydroxypiperidin-1-yl)-5-methyl-1-oxo-1H,5H-benzo[i,j]quinolizine-2-carboxylic Acid L-Arginine Salt Hydrate To a three-necked round bottom flask fitted on oil bath and equipped with magnetic stirrer and reflux condenser; S-(−)-9-fluoro-6,7-dihydro-8-(4-hydroxypiperidin-1-yl)-5-methyl-1-oxo-1H,5H-benzo[i,j]quinolizine-2-carboxylic acid (2 gm, 5.55 mmoles) and L-arginine (1.44 gm, 8.27 mmole) were charged in a mixture of acetone (10 ml) and water (5 ml). The reaction mixture was slowly heated under stirring at 50 to 60° C. temperature to obtain a clear solution. The solution was allowed to cool to 30–35° C. and then was further cooled in ice bath. The solid separated was filtered at suction and was washed with a cold mixture of acetone (10 ml) and water (5 ml). The crystalline solid was dried in a vacuum oven at 65–70° C. to afford 2.4 gm (81%) dry compound, $[\alpha]_D^{25}$ value calculated on anhydrous basis is 183° (c=1, methanol).

EXAMPLE 3

Preparation of S-(−)-9-Fluoro-6,7-dihydro-8-(4-hydroxypiperidin-1-yl)-5-methyl-1-oxo-1H,5H-benzo[i,j]quinolizine-2-carboxylic Acid L-Arginine Salt Hydrate To the suspension of S-(−)-9-fluoro-6,7-dihydro-8-(4-hydroxypiperidin-1-yl)-5-methyl-1-oxo-1H,5H-benzo[i,j]quinolizine-2-carboxylic acid (100 gm, 0.278 mole) in acetone (300 ml) was added L-arginine (45 gm, 0.258 mole) and water (250 ml). The mixture was heated to 50 to 60° C. temperature for one hour to obtain a clear solution. Activated charcoal (5 gm) was added to the solution and the solution was filtered hot. To the filtrate was added acetone (700 ml) and the mixture was cooled gradually to 30 to 35° C. temperature, a solid crystallized out which was filtered and washed with aqueous acetone and finally with acetone. On drying in vacuum oven at 65 to 70° C. S-(−)-9-fluoro-6,7-dihydro-8-(4-hydroxypiperidin-1-yl)-5-methyl-1-oxo-1H,5H-benzo[i,j]quinolizine-2-carboxylic acid, L-arginine salt was obtained as a crystalline powder weighing 137 gm (92%). $[\alpha]_D^{25}$ value calculated on anhydrous basis is −183.34° (c=1, methanol).

EXAMPLE 4

Preparation of S-(−)-9-Fluoro-6,7-dihydro-8-(4-hydroxypiperidin-1-yl)-5-methyl-1-oxo-1H,5H-benzo[i,j]quinolizine-2-carboxylic Acid L-Arginine Salt Hydrate To a three necked 1 lit. round bottom flask fitted on the water bath and equipped with mechanical stirrer, thermometer pocket and reflux condenser was charged S-(−)-9-fluoro-6,7-dihydro-8-(4-hydroxypiperidin-1-yl)-5-methyl-1-oxo-1H,5H-benzo[i,j]quinolizine-2-carboxylic acid (25 gm, 69.44 mmole) and acetonitrile (75 ml). Stirring was started and to the stirred suspension was charged powdered L-arginine (12.16 gm, 69.88 mmole) followed by distilled water (60 ml). The reaction mixture was stirred at the temperature between 50 to 60° C. for one hour to obtain a homogeneous clear solution. Clear reaction mixture was then charged 225 ml fresh acetonitrile under stirring. Activated charcoal (3 gm) was added to the solution and the solution was filtered hot. Filtrate was allowed to cool to 30 to 35° C. under stirring. The reaction mixture was stirred for additional 3 hours at this temperature. The crystalline solid was filtered at suction and the wet cake was washed with 25 ml acetonitrile. Resulting crystalline solid was dried under vacuum at 65 to 70° C. to furnish 34.5 gm (93%) title compound, $[\alpha]_D^{25}$ value calculated on anhydrous basis is −183.99° (c=1, methanol).

EXAMPLE 4-A

Preparation of S-(−)-9-Fluoro-6,7-dihydro-8-(4-hydroxypiperidin-1-yl)-5-methyl-1-oxo-1H,5H-benzo[i,j]quinolizine-2-carboxylic Acid L-Arginine Salt A mixture of the two enantiomers [88.24% S-(−)-isomer and 11.76% R-(+)-isomer] of 9-fluoro-6,7-dihydro-8-(4-hydroxypiperidin-1-yl)-5-methyl-1-oxo-1H,5H-benzo[i,j]quinolizine-2-carboxylic acid (1.5 gm, 4.16 mmol) was suspended in a mixture of acetone (4.5 ml) and water (3.8 ml). To the stirred suspension L-arginine (0.725 gm, 4.16 mmol) was added. The mixture was warmed to a temperature between 50–60° C. to obtain a clear solution. Acetone (11 ml) was added to the solution, which was then cooled to 30–35 ° C. and stirred for 2 hours. The crystalline solid obtained was filtered under suction and the residue was washed with 2 ml acetone. The resulting solid was dried to furnish 1.8 gm (92%) of the title compound.

Chiral analysis of the crystals were performed by chromatography on an analytical chiral column. The optical purity of the crystals was found to be 97.06%. The cystallinity was determined by powder X-ray diffraction.

EXAMPLE 4-B

The above experiment was repeated on the mixture of enantiomer having optical purity 89% S-(−)-isomer and 11%

R-(+)-isomer of 9-fluoro-6,7-dihydro-8-(4-hydroxypiperidin-1-yl)-5-methyl-1-oxo 1H,5H-benzo[i,j]quinolizine-2-carboxylic acid using acetonitrile instead of acetone in accordance with the conditions and quantities described in Example 4-A to provide the product of which optical purity was enhanced to 98% as shown by chiral chromatography.

EXAMPLE 5

Preparation of S-(−)-9-Fluoro-6,7-dihydro-8-(4-hydroxypiperidin-1-yl)-5-methyl-1-oxo-1H,5H-benzo[i,j]quinolizine-2-carboxylic Acid D-Arginine Salt To a suspension of S-(−)-9-fluoro-6,7-dihydro-8-(4-hydroxypiperidin-1-yl)-5-methyl-1-oxo-1H,5H-benzo[i,j]quinolizine-2-carboxylic acid (1 g, 2.77 mmol) in methanol (50 ml) was charged a solution of D-arginine (0.483 g, 2.77 mmol) in 10 ml water at 60–65° C. The clear solution obtained was stirred for 15 minutes at 60–65° C. The reaction mixture was evaporated to dryness under reduced pressure to give 1.3 g (88%) of the title compound, m.p. 241–243° C., $[\alpha]_D^{25}$=−174.4° (c=1, methanol).

EXAMPLE 6

Preparation of R-(+)-9-Fluoro-6,7-dihydro-8-(4-hydroxypiperidin-1-yl)-5-methyl-1-oxo-1H,5H-benzo[i,j]quinolizine-2-carboxylic Acid L-Arginine Salt This compound may be prepared according to the procedure described in Example 5 using R-(+)-9-fluoro-6,7-dihydro-8-(4-hydroxypiperidin-1-yl)-5-methyl-1-oxo-1H,5H-benzo[i,j]quinolizine-2-carboxylic acid instead of S-(−)-9-fluoro-6,7-dihydro-8-(4-hydroxypiperidin-1-yl)-5-methyl-1-oxo-1H,5H-benzo[i,j]quinolizine-2-carboxylic acid and L-arginine instead of D-arginine.

EXAMPLE 7

Preparation of R-(+)-9-Fluoro-6,7-dihydro-8-(4-hydroxypiperidin-1-yl)-5-methyl-1-oxo-1H,5H-benzo[i,j]quinolizine-2-carboxylic Acid D-Arginine Salt This compound may be prepared following Example 6 by substituting an equivalent amount of D-arginine for L-arginine. m.p. (DSC) 232.0° C., $[\alpha]_D^{25}$=+171.4° (c=1, methanol).

EXAMPLE 8

Preparation of RS-(±)-9-Fluoro-6,7-dihydro-8-(4-hydroxypiperidin-1-yl)-5-methyl-1-oxo-1H,5H-benzo[i,j]quinolizine-2-carboxylic Acid L-Arginine Salt This compound may be prepared following Example 6 by substituting RS-(±)-9-fluoro-6,7-dihydro-8-(4-hydroxypiperidin-1-yl)-5-methyl-1-oxo-1H,5H-benzo[i,j]quinolizine-2-carboxylic acid for R-(+)-9-fluoro-6,7-dihydro-8-(4-hydroxypiperidin-1-yl)-5-methyl-1-oxo-1H,5H-benzo[i,j]quinolizine-2-carboxylic acid.

EXAMPLE 9

Preparation of RS-(±)-9-Fluoro-6,7-dihydro-8-(4-hydroxypiperidin-1-yl)-5-methyl-1-oxo-1H,5H-benzo[i,j]quinolizine-2-carboxylic Acid D-Arginine Salt This compound may be prepared following Example 8 by substituting an equivalent amount of D-arginine for L-arginine. M.p (DSC) 234.8° C.

The crystalline S-(−)-9-fluoro-6,7-dihydro-8-(4-hydroxypiperidin-1-yl)-5-methyl-1-oxo-1H,5H-benzo[i,j]quinolizine-2-carboxylic acid L-arginine salt prepared according to Examples 1–4B possesses the following properties:

a) Crystalline form, with a degree of crystallinity as determined by X-ray powder diffraction and as shown in FIG. 1.

b) A thermogram as determined by Differential scanning calorimetry and as shown in FIG. 2.

c) Particle size measured as mean mass diameter (MMD) of less than or equal to 40 μm, as determined by laser diffraction technique.

d) Bulk density of 0.57 g/cm³ (untapped) and 0.64 g/cm³ (tapped) as shown in FIG. 3. Untapped density is defined as 25 gm/untapped volume. The results are provided in FIG. 3. Tapped density is defined as 25 gm/tapped volume. The results are provided in FIG. 3.

e) Hygroscopicity of 3% increase of weight upon storage for 14 days up to 22% relative atmospheric humidity at 30° C. as determined gravimetrically.

f) Water content of between 4.0% to 4.4% by weight as determined by titration according to Karl Fischer.

g) A content of acetone of 0.011% by weight, or of acetonitrile of 0.03% by weight, as determined by gas chromatography.

TEST EXAMPLE 1

X-ray Diffraction Analysis 300 mg each of S-(−)-9-fluoro-6,7-dihydro-8-(4-hydroxypiperidin-1-yl)-5-methyl-1-oxo-1H,5H-benzo[I,j]quinolizine-2-carboxylic acid L-arginine salt prepared as in Example 1 was thinly spread on a sample holder. X-ray diffraction analyses (40 kv×40 mA Rigaku D/max 2200) were performed under the conditions listed below:

Scan speed 5°/min

Sampling time 7 min

Scan mode: continuous

2θ/θ reflection

Cu target (Ni filter)

Results of the X-ray diffraction analysis on the crystalline form is depicted in FIG. 1.

TEST EXAMPLE 2

Thermal Analysis of the S-(−)-9-Fluoro-6,7-dihydro-8-(4-hydroxypiperidin-1-yl)-5-methyl-1-oxo-1H,5H-benzo[I,j]quinolizine-2-carboxylic Acid L-Arginine Salt For the Differential Scanning Calorimetry, METTLER TOLEDO STAR system was used. 5 to 6 mg of the sample was weighed into the aluminum pan, which was then press sealed with an aluminium lid. After three tiny needle holes were made on the lid the sample was tested by heating from (30° C.) to (300° C.) at a rate of 10° C./min. Result can be seen from FIG. 2. There is an exothermic peak at around 194.93° C. and an endothermic peak at 251.26° C., other endothermic peaks are observable at 87.83° C., 98.04° C., 144.03° C. and 159.14° C.

TEST EXAMPLE 3

Bulk Density Determination

For untapped and tapped density determination Bulk Density Apparatus (R.V. Electronics, Mumbai) was used. 25 g of the sample was slowly poured into a dry clean stoppered measuring cylinder and filled volume was measured to obtain untapped density.

Untapped density=25 g/untapped volume.

Then the measuring cylinder was fixed to Bulk Density Apparatus and sample was tapped (150 times) and volume was measured to furnish the tapped volume.

Tapped density=25 g/Tapped volume.

The results are shown in FIG. 3.

TEST EXAMPLE 4

Mean Mass Diameter Determination

For mean mass diameter Master Sizer of Malvern Instrument LTD U.K. was used under the conditions listed below:

Lens/Focus: 300 mm

Solvent: Hexane

Analysis model: Polydisperse

Obstruction value: 20–23%

The particle size measured as mean mass diameter of the crystalline form of S(-)-9-fluoro-6,7-dihydro-8-(4-hydroxypiperidin-1-yl)-5-methyl-1-oxo-1H,5H-benzo[i,j]quinolizine-2-carboxylic acid L-arginine salt of the invention from four different samples made by the procedure described in example 1 is as given in Table 1.

TABLE 1

| Sample No. | Mean mass diameter ($\mu$m) |
|---|---|
| 1 | 32.92 |
| 2 | 24.22 |
| 3 | 34.51 |
| 4 | 39.07 |

The mean value is 32.68 $\mu$m.

What is claimed is:

1. A S-(-)-9-fluoro-6,7-dihydro-8-(4-hydroxypiperidin-1-yl)-5-methyl-1-oxo-1H,5H-benzo[i,j]quinolizine-2-carboxylic acid L-arginine salt having the following X-ray powder diffraction data: (2θ): 14.02±0.2, 14.82±0.2, 19.28±0.2, 22.12±0.2, 22.96±0.2, 23.46±0.2, 28.36±0.2.

2. The S-(-)-9-fluoro-6,7-dihydro-8-(4-hydroxypiperidin-1-yl)-5-methyl-1-oxo-1H,5H-benzo[i,j]quinolizine-2-carboxylic acid L-arginine salt according to claim 1, wherein the mean mass diameter as determined by laser diffraction technique is less than or equal to 40 $\mu$m.

3. The S-(-)-9-fluoro-6,7-dihydro-8-(4-hydroxypiperidin-1-yl)-5-methyl-1-oxo-1H,5H-benzo[i,j]quinolizine-2-carboxylic acid L-arginine salt according to claim 2, wherein the diameter is less than 32 $\mu$m.

4. The S-(-)-9-fluoro-6,7-dihydro-8-(4-hydroxypiperidin-1-yl)-5-methyl-1-oxo-1H,5H-benzo[i,j]quinolizine-2-carboxylic acid L-arginine salt according to claim 1, wherein the density is between 0.57 g/cm$^3$ (untapped) and 0.64 g/cm$^3$ (tapped).

5. The S-(-)-9-fluoro-6,7-dihydro-8-(4-hydroxypiperidin-1-yl)-5-methyl-1-oxo-1H,5H-benzo[i,j]quinolizine-2-carboxylic acid L-arginine salt according to claim 1, wherein the water content is between 4.0 and 4.4% by weight as determined by titration according to Karl Fischer.

6. The S-(-)-9-fluoro-6,7-dihydro-8-(4-hydroxypiperidin-1-yl)-5-methyl-1-oxo-1H,5H-benzo[i,j]quinolizine-2-carboxylic acid L-arginine salt according to claim 1, having an organic solvent content less than 0.05% by weight as determined by gas chromatography.

7. A process for the manufacture of S-(-)-9-fluoro-6,7-dihydro-8-(4-hydroxypiperidin-1-yl)-5-methyl-1-oxo-1H, 5H-benzo[i,j]quinolizine-2-carboxylic acid L-arginine salt according to claim 1 comprising the steps of:

a) dissolving S-(-)-9-fluoro-6,7-dihydro-8-(4-hydroxypiperidin-1-yl)-5-methyl-1-oxo-1H,5H-benzo[i,j]quinolizine-2-carboxylic acid with L-arginine in acetone or acetonitrile, and water to form a solution;

b) heating the solution of step a) at 50° to 60° C.;

c) cooling the solution to 30–35° C. to provide a crystalline substance;

d) isolating the crystalline form of S-(-)-9-fluoro-6,7-dihydro-8-(4-hydroxypiperidin-1-yl)-5-methyl-1-oxo-1H,5H-benzo[i,j]quinolizine-2-carboxylic acid L-arginine salt at <35° C. by filtration; and e) purifying and drying the crystalline form of S-(-)-9-fluoro-6,7-dihydro-8-(4-hydroxypiperidin-1-yl)-5-methyl-1-oxo-1H,5H-benzo[i,j]quinolizine-2-carboxylic acid L-arginine salt.

8. A solid composition comprising S-(-)-9-fluoro-6,7-dihydro-8-(4-hydroxypiperidin-1-yl)-5-methyl-1-oxo-1H, 5H-benzo[i,j]quinolizine-2-carboxylic acid L-arginine salt according to claim 1 and a solid carrier, diluent, or excipient.

9. A method for treating a disease caused by a microbial infection in a mammal comprising administering an effective amount of S-(-)-9-fluoro-6,7-dihydro-8-(4-hydroxypiperidin-1-yl)-5-methyl-1-oxo-1H,5H-benzo[i,j]quinolizine-2-carboxylic acid L-arginine salt according to claim 1, to the mammal in need thereof.

10. The process according to claim 7, wherein the percentage of water in the solvent mixture is 20%–80%.

11. A solid composition prepared by a process comprising combining S-(-)-9-fluoro-6,7-dihydro-8-(4-hydroxypiperidin-1-yl)-5-methyl-1-oxo-1H,5H-benzo[i,j]quinolizine-2-carboxylic acid L-arginine salt according to claim 1 and a solid carrier, diluent, or excipient.

* * * * *